(12) United States Patent
Jaeger et al.

(10) Patent No.: US 9,675,440 B2
(45) Date of Patent: Jun. 13, 2017

(54) BAND-LIKE STRUCTURE FOR THE AUGMENTATION OF A LIGAMENT

(71) Applicant: FEG Textiltechnik Forschungs- und Entwicklungsgesellschaft mbH, Aachen (DE)

(72) Inventors: Wolfram Jaeger, Duesseldorf (DE); Andreas Muellen, Aachen (DE); Boris Obolenski, Aachen (DE)

(73) Assignee: FEG Textiltechnik Forschungs—und Entwicklungsgesellschaft mbH, Aachen (DE)

( * ) Notice: Subject to any disclaimer, the term of this patent is extended or adjusted under 35 U.S.C. 154(b) by 104 days.

(21) Appl. No.: 13/923,957

(22) Filed: Jun. 21, 2013

(65) Prior Publication Data

US 2013/0345810 A1 Dec. 26, 2013

(30) Foreign Application Priority Data

Jun. 22, 2012 (DE) .................... 20 2012 006 023 U

(51) Int. Cl.
| | | |
|---|---|---|
| A61F 2/08 | (2006.01) | |
| A61F 2/00 | (2006.01) | |
| D04B 21/20 | (2006.01) | |

(52) U.S. Cl.
CPC ............ *A61F 2/08* (2013.01); *A61F 2/0045* (2013.01); *D04B 21/20* (2013.01); *A61F 2002/0068* (2013.01); *A61F 2250/0007* (2013.01); *A61F 2250/0014* (2013.01); *A61F 2250/0039* (2013.01); *A61F 2250/0085* (2013.01); *D10B 2403/0311* (2013.01); *D10B 2509/08* (2013.01)

(58) Field of Classification Search
USPC .................. 623/13.11–14.11; 600/29–32, 37
See application file for complete search history.

(56) References Cited

U.S. PATENT DOCUMENTS

| | | |
|---|---|---|
| 2,006,229 A | 6/1935 | Cone et al. |
| 2,009,319 A | 7/1935 | James |

(Continued)

FOREIGN PATENT DOCUMENTS

| | | |
|---|---|---|
| DE | 102004015720 | 10/2005 |
| EP | 1600118 | 11/2005 |

(Continued)

OTHER PUBLICATIONS

Mühl et al., "New Objective Measurement to Characterize the Porosity of Textile Implants," Journal of Biomedical Materials Research Part B: Applied Biomaterials, 2007, 84B (1), pp. 176-183.

(Continued)

*Primary Examiner* — Yashita Sharma
(74) *Attorney, Agent, or Firm* — Pauly Devries Smith & Deffner, LLC

(57) ABSTRACT

The invention relates to a band-like structure for the augmentation of a ligament, comprising a central section for fastening to an organ of the true pelvis, said central section having a central knit fabric with a central warp direction, a lateral section for fastening to a suspension surface and a plurality of threads, which are connected to the central section and the lateral section. It is proposed that the central knit fabric comprises the plurality of threads.

23 Claims, 1 Drawing Sheet

(56) References Cited

U.S. PATENT DOCUMENTS

| | | |
|---|---|---|
| 6,575,897 B1 | 6/2003 | Ory et al. |
| 7,198,597 B2 * | 4/2007 | Siegel et al. .................... 600/30 |
| 8,016,741 B2 | 9/2011 | Weiser et al. |
| 2006/0079953 A1 * | 4/2006 | Gregorich et al. .......... 623/1.15 |
| 2008/0300683 A1 * | 12/2008 | Altman et al. ............. 623/13.11 |
| 2009/0259092 A1 | 10/2009 | Ogdahl et al. |
| 2011/0166673 A1 * | 7/2011 | Patel et al. ................. 623/23.72 |

FOREIGN PATENT DOCUMENTS

| | | |
|---|---|---|
| EP | 2250973 | 11/2010 |
| GB | 2474866 | 5/2011 |
| WO | 03037215 | 12/2003 |
| WO | 2011115340 | 9/2011 |

OTHER PUBLICATIONS

Search Report for German Application No. DE202012006023.6 corresponding to U.S. Appl. No. 13/923,957, mailed Mar. 2, 2013, 5 pages.

Search Report, for European Patent Application No. 13003000 corresponding to U.S. Appl. No. 13/923,957, mailed Oct. 8, 2013 (2 pages).

* cited by examiner

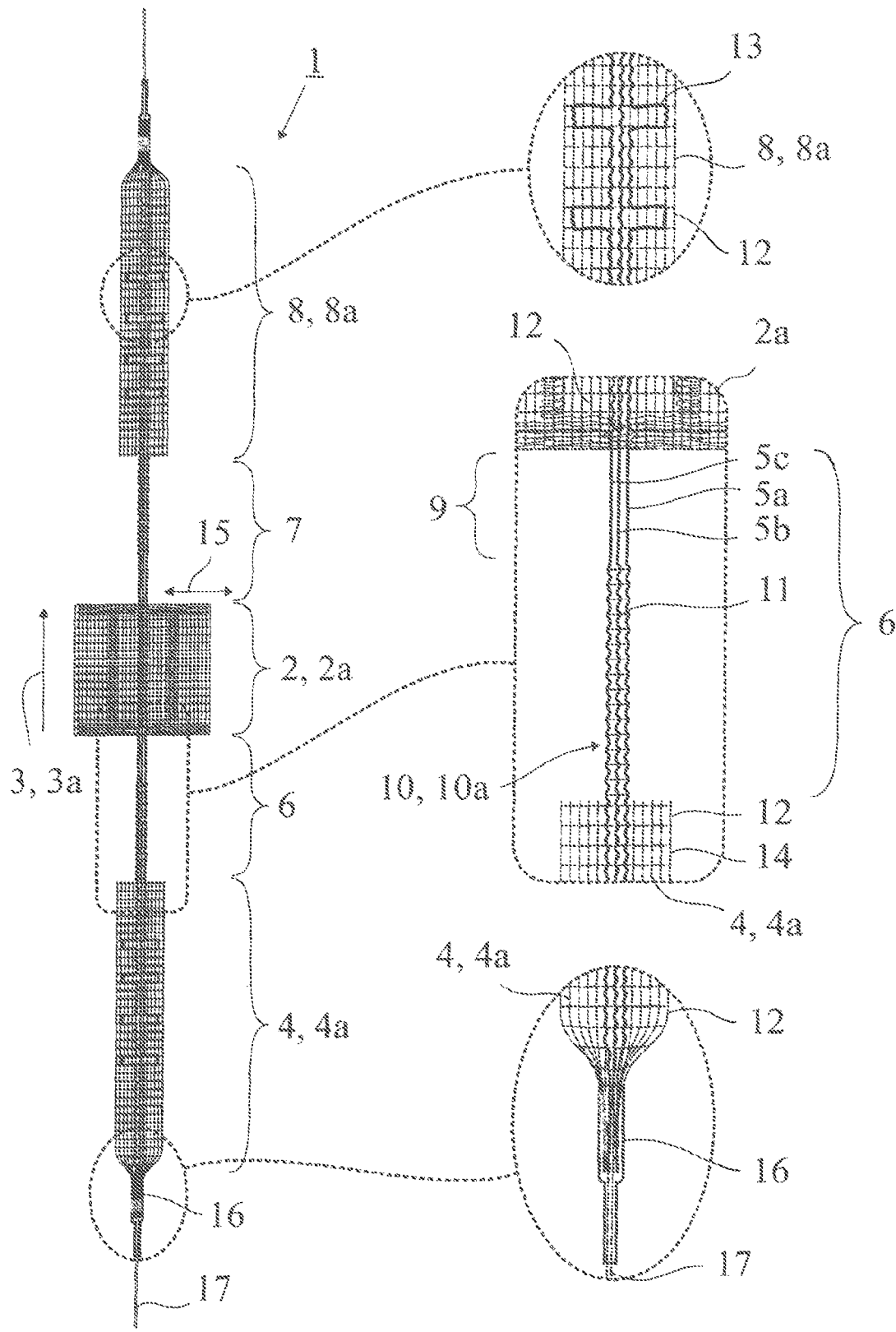

BAND-LIKE STRUCTURE FOR THE AUGMENTATION OF A LIGAMENT

CLAIM OF PRIORITY

This application claims the benefit of German Patent Application No. DE 20 2012 006 023.6, filed Jun. 22, 2012, the disclosure of which is incorporated by reference herein in its entirety.

FIELD OF THE INVENTION

The invention relates to a band-like structure for the augmentation of a ligament and a method for the manufacture of such a band-like structure.

BACKGROUND

The present band-like structure serves as a medical implant for the reinforcement and/or the replacement of ligaments in the pelvic region. Said ligaments in the true pelvis often become weaker or completely fail with increasing age, which in the case of female patients may lead to a lowering of the uterus or the vagina. From a certain severity onwards, reference is made even to a corresponding prolapse. This displacement of the uterus or the vagina often also leads to a displacement of the position of the urinary bladder in the sub-peritoneal space, or to a variation of the forces which act on the urinary bladder in comparison to the healthy state. Incontinence is then often the consequence.

From the prior art it is known to treat such displacements or prolapses with an artificial suspension of the affected organs, which were previously retained by the endogenous ligaments, on anatomically suitable fastening locations.

U.S. Pat. No. 6,575,897, which is considered the closest prior art, thus discloses a suspension device having a two-dimensional central textile and two also two-dimensional lateral textiles made from the same textile material, which are interconnected by a string-like band, which is also made from the identical textile material. The band is sewn or welded onto the central textile—which may also be referred to as central section—and onto both lateral textiles—correspondingly referred to as lateral sections. During a surgical procedure, the central textile is now fastened to the organ to be supported. This location may also be referred to as traction point. As a rule, this is usually either the uterus or, in the frequent case in which a hysterectomy has already been performed, the remaining cervix or the vaginal stump. The two lateral textiles are then guided out of the sub-peritoneal space through openings in the peritoneum in order to be subsequently fastened to a suitable fastening location, which often is osseous, such as, for example, the sacral bone. In this manner, the affected organ is returned to its original position and any possible displacement ruled out again.

However, this suspension device for the augmentation of ligaments has several significant disadvantages. In order for a contact which is to be load-bearing in the long term to develop on the traction point corresponding to the location to be supported, for example the cervix, and on the fastening locations, in this case the sacral bone, meshes in the textile which are as large as possible are of advantage, since they favor the ingrowth of tissue into the meshes of the textile. However, the effective porosity of the structure is very considerably reduced by the superimposition of the two textiles, especially in the sections where, according to the prior art, the band is attached to the central textile or the lateral textiles. It is obvious that no identical overlaying of the meshes of the band with the meshes of the central textile or those of the lateral textiles can be achieved in practice, which is why the porosity created at these locations is for this reason alone, in principle, only half of that compared to the state in which there is no superimposition.

It is to be noted in this context that it is not relevant to the porosity, being fundamentally defined as the percentage of open surface in relation to the total surface of the textile, what porosity the respective textile has in its original state, but rather what the effective porosity is after the application of said textile. The porosity in the original state is, for example, diminished in that inevitably granuloma and scar tissue envelop the individual strands of the textile because of the response of the body to foreign material, as a result of which open surface is naturally lost. In the extreme case, a complete closure of the net meshes which form the pores may occur as a result of this reaction. The term effective porosity, which is relevant in this case, is known to the person skilled in the art from the essay "New Objective Measurement to Characterize the Porosity of Textile Implants" by Muhl, Binnebosel, Klinge and Goedderz (Journal of Biomedical Materials Research Part B: Applied Biomaterials, 2007.84B(1): p. 176/183), to which specific reference is made here.

The superimposition of the two textile net structures of the central textile and/or the lateral textile and the band thus leads to a disproportionately high reduction of the effective porosity in the mentioned sense, as a result of which the ingrowth of the implant into the tissue is made considerably difficult especially at the traction point.

This problem is additionally aggravated in that the superimposition of the textiles not only affects the porosity, but in these sections also the bending property of the material as a whole. As a result, an exact adaption to the tissue is no longer so easily possible, something that would, however, also be of advantage to the already mentioned ingrowth of the tissue into the implant.

For these two reasons, a poorer hold is provided exactly at the particularly important locations at which the intrinsic contact with the fraction point and the fastening locations is made than in the peripheral regions of the central textile or the lateral textiles.

In addition to this, the fastening of the band on the central textile and on both lateral textiles must hold unconditionally throughout the entire service life of the suspension device. In the case of a detachment of the welded or sutured connection, for whatever reason, from even just one of these locations, the organ can no longer be supported and the fundamentally same situation occurs as prior to the use of the suspension device, including the corresponding necessity for another surgical procedure to be carried out on the patient.

Furthermore, the known textile material has no provision against any constriction. The suspension device is exposed not only to a constant tensile load, but also to a dynamic tensile load which results from, for example, a variation in the filling level of the urinary bladder and the body movements of the patient. This tensile load on the suspension device may, however, lead to a constrictive deformation of the individual meshes of the textile material. As a result of such a constriction, not only are the meshes diminished in their area size, which leads to a corresponding reduction of the effective porosity, but any intergrowth already established between tissue and the individual meshes is also severed again and torn open. This, too, slows the process of ingrowth and reduces the quality of the fastening of the suspension device.

Consequently, the object underlying the invention is that of refining and further developing the band-like structure for the augmentation of a ligament according to the prior art, and its corresponding method of manufacture, in such a manner that an improved connection is achieved between said band-like structure and the tissue at the contact locations.

SUMMARY

The aforementioned object is achieved with a band-like structure for the augmentation of a ligament comprising a central section for fastening to an organ of the true pelvis, said central section having a central knit fabric with a central warp direction; a lateral section for fastening to a suspension surface; and a plurality of threads which are connected to the central section and the lateral section; wherein the central knit fabric comprises the plurality of threads.

With reference to the method of manufacture, the aforementioned object is achieved by the use of a galloon machine.

It is a substantial insight that an improved connection between the band-like structure to be implanted and the location of the tissue to be suspended can be achieved in that the band-like part, which is intended to constitute the connection between the location to be suspended—the traction point—and the fastening locations, and the central section for connecting this very traction point consist of one and the same warp-knitted textile. This band-like part comprises a plurality of threads. The irregularity in the textile structure, which results from the subsequent fastening of the band-like textile on the actual, two-dimensional contact part according to the prior art, and the disadvantages which have just been described and are associated with said irregularity, can then be completely avoided.

In this manner, the central section can be configured as a knit fabric which has been optimized for contact with the tissue and is not adversely affected in this respect by other superimposed structures. The knit fabric according to the invention refers to a warp knit made using crochet galloon technology. Such a knit fabric can be made on a crochet galloon machine, that is to say a warp knitting machine having a weft insertion system.

In the sense of the invention, central warp direction refers to the warp direction of the central knit fabric. This warp direction corresponds to the direction of manufacture of the textile in the crochet galloon machine, that is to say the direction in which the knitting needles progress in the arrangement of the warp threads of the warp knit. The weft direction is orthogonal to the warp direction in the plane of the corresponding knit fabric, said weft direction corresponding to the fundamental orientation of the weft threads. In this context, the two conceivable orthogonal directions in relation to the warp direction in the plane of the knit fabric are to be understood to be weft direction.

The inclusion of the plurality of threads by the central knit fabric is to be understood such that these threads are in one form or another an integral part of the knit fabric. This is exactly the case when each individual thread of the plurality of threads has been used either as warp thread or as weft thread in the manufacture of the warp knit, wherein some threads may have also been used as weft threads and others as warp threads. Each one of these threads may consist of a multifilament or a monofilament.

An extension of some of the threads used for the manufacture of this knit fabric may then be correspondingly used as band-like structure for connecting the central and lateral sections. The intrinsic contact location is thus entirely unaffected by this measure—i.e. the alternative application of the threads used.

As has already been described, the suspension device is regularly exposed to tensile load. It can be ensured by means of the invention that such a tensile load is absorbed by the mentioned threads and also transmitted through the knit fabric which forms the central section by means of these very threads, without any substantial deformation of the central section occurring. Above all, no constriction of the meshes of the central section occurs, such that the high effective porosity of the central section can be preserved.

The implementation in the form of a knit fabric further enables the integral manufacture of this complex structure on a crochet galloon machine.

The preferred embodiments describe a connecting section between the central section, which is intended to be in contact with the traction point, and the lateral section for contact with the fastening locations. This connecting section should intentionally not form any connection with tissue but rather bridge the distance between the traction point and the fastening locations in a manner that is as contact-free as possible. The preferred embodiments provide that the connecting section at least substantially consists of the threads which connect the central section and the lateral section. This achieves that tensile forces on the band-like structure according to the invention are completely transmitted from one lateral section to the central section and optionally to further existing lateral sections by the mentioned threads. In this manner, especially these threads can be configured to absorb the tensile forces. Furthermore, deformation and constricting effects in the meshes of the band-like structure are avoided.

Since the band-like structure is inserted in a rolled-up state into the sub-peritoneal space through a hole, it is quite possible that in the course of the subsequent spreading out of the central section and the lateral sections these are, with regard to their connection, arranged contorted in relation to one another. For this reason, a special contortion section is preferably provided in the band-like structure, said contortion section being able to locally absorb any such contortion without forces being exerted on the central section or the lateral sections, as a result of which said sections could detach from their corresponding contact surface.

A preferred embodiment provides that also the lateral sections each have a warp knit which comprises the plurality of threads in the same sense as the central section. The advantages described of the central section according to the invention thus also apply to the lateral sections.

A preferred embodiment which particularly simplifies an ad hoc customization of the length of the band-like structure is described.

As a result of the preferred longitudinal orientation of the rectangular mesh openings of the central section in warp direction according to a preferred embodiment, the porosity is increased—for example by dispensing with half of the transverse webs in the case of square mesh openings—without negatively affecting the response of the band-like structure to tensile load.

An embodiment optimizes the insertion of the band-like structure into the sub-peritoneal space.

A particularly preferred embodiment enables the further success of the treatment using the implanted band-like structure to be monitored post-operatively. In an embodiment, the invention provides for a band-like structure for the augmentation of a ligament, comprising a central section for fastening to an organ of the true pelvis, said central section having a central knit fabric with a central warp direction; a lateral section for fastening to a suspension surface; and a plurality of threads which are connected to the central section and the lateral section; wherein the central knit fabric comprises the plurality of threads.

In one embodiment, the band-like structure has a connecting section, the connecting section comprising the plurality of threads, wherein the connecting section is located between the central section and the lateral section such that a tensile force exerted on the central section and the lateral section is at least sectionally completely transmitted by the connecting section.

In one embodiment, the band-like structure comprises a second connecting section and a second lateral section; wherein a connecting section is respectively located between the central section and the lateral sections such that a tensile force exerted on the two lateral sections is at least sectionally completely transmitted by the connecting sections.

In one embodiment, the connecting section comprises a contortion section which comprises the plurality of threads.

In one embodiment, the plurality of threads sectionally forms a textile band in which the plurality of threads is interconnected by binding fibers.

In one embodiment, the connecting section comprises a transitional section which consists of the textile band.

In one embodiment, the plurality of threads forms warp threads in the central knit fabric.

In one embodiment, the lateral section comprises a lateral knit fabric.

In one embodiment, the plurality of threads is arranged such that it forms markings.

In one embodiment, the band-like structure comprises a common warp direction.

In one embodiment, the central section comprises rectangular mesh openings.

In one embodiment, the central section, the lateral section and the plurality of threads, in particular also the connecting section, consist of non-absorbable, bio-stable polyvinylidene fluoride.

In one embodiment, the band-like structure comprises a tube-shaped insertion aid, which is fastened to the lateral section.

In one embodiment, the band-like structure further comprises at least one additive which is visible in magnetic resonance tomography.

In one embodiment, the manufacture of a band-like structure uses a crochet galloon machine.

In one embodiment, the lateral section is at least sectionally completely transmitted by the connecting section, by the plurality of threads.

In one embodiment, the tensile force exerted on the two lateral sections is at least sectionally completely transmitted by the connecting sections by the plurality of threads.

In one embodiment, the plurality of threads is separately guided within the contortion section.

In one embodiment, the lateral knit fabric comprises the lateral knit fabric, said lateral knit fabric comprising the plurality of threads.

In one embodiment, the plurality of threads forms warp threads in the lateral knit fabric, in particular that the lateral knit fabric comprises the binding fibers.

In one embodiment, the markings are spaced in a regular manner, for identifying cutting or connecting locations.

In one embodiment, the plurality of threads form warp threads along the band-like structure, in particular, that all edges of the band-like structure along the common warp direction are genuine edges.

In one embodiment, the rectangular mesh openings are oriented along the central warp direction, in particular that the rectangular mesh openings are longer in the central warp direction than in a weft direction of the central section.

In one embodiment, the insertion aid is connected to the plurality of threads.

BRIEF DESCRIPTION OF THE FIGURES

In the following, the invention is described in more detail with reference to a drawing which illustrates only one exemplary embodiment. In the drawing:

FIG. 1 shows a band-like structure for the augmentation of a ligament according to the proposal in a plan view prior to implantation.

DETAILED DESCRIPTION

The band-like structure 1 according to the invention illustrated in the drawing, and used for the augmentation of a ligament, is suited for the treatment of a lowering or a prolapse of an organ in the true pelvis, in particular the uterus or the vagina. In this case the ligaments, which should retain the organ concerned in the healthy state, are supported or replaced by the band-like structure 1.

As is illustrated in FIG. 1, the band-like structure 1 according to the invention comprises a central section 2 for fastening to an organ of the true pelvis. The fastening to the organ may occur by stapling, suturing or in another manner. The central section 2 is intended to ingrow into the tissue in the medium term. The location of the organ to which the central section 2 is fastened represents the traction point in the sense that this location is to be supported by the band-like structure 1 such that a tensile force is exerted on this location.

The central section 2 has a central knit fabric 2a—which is a warp knit—having a central warp direction 3. The central warp direction 3 simply corresponds to the warp direction of the warp knit which is the central knit fabric 2a.

The band-like structure 1 according to the invention further comprises a lateral section 4 for fastening to a suspension surface. This suspension surface represents that fixed fastening location which supports the traction point via the band-like structure 1. As a rule, the fastening location is an osseous or bone-related structure, such as, for example, a location on the sacral bone or the coccyx. Apart from a fastening to the bone itself, a fastening to the periosteum surrounding the bone is equally feasible. Beyond this, the fastening location may also be chosen to be on a ligament. According to the invention, the band-like structure 1 further comprises a plurality of threads 5a, 5b, 5c which are connected to the central section 2 and the lateral section 4. In the case illustrated here, there are three threads 5a, 5b, 5c.

According to the invention, all further details pertaining to the arrangement or the relation of the plurality of threads 5a, 5b, 5c to one another are freely selectable. These may extend parallel and in one line or in each case in an individually meandering manner. They may be without any connection to one another, interlaced with one another or at least sectionally linked to one another by means of further fibers or threads.

According to the invention, it is now further provided that the central knit fabric 2a comprises the plurality of threads 5a, 5b, 5c. Each individual thread 5a, 5b, 5c is thus integrated into the central knit fabric 2a as warp or weft thread. In this manner, there are no locations of contact in the true sense between the plurality of threads 5a, 5b, 5c and the central section 2. A tensile force on the plurality of threads 5a, 5b, 5c therefore acts at exactly defined locations on the central section 2.

It is in this case preferred that each individual thread of the plurality of threads 5a, 5b, 5c is formed as a braiding of monofilaments.

In a preferred embodiment, the band-like structure 1 has a connecting section 6 which comprises the plurality of threads 5a, 5b, 5c. In this case, the connecting section 6 is located between the central section 2 and the lateral section 4 such that a tensile force which is exerted on the central section 2 and the lateral section 4 is at least sectionally completely transmitted by the connecting section 6. In other words, this means that in the event of a tensile force being exerted on the central section 2 and the lateral section 4, the transmission path of said tensile force from the central section 2 to the lateral section 4 (or vice versa) at least comprises a stage onto which the tensile force is transmitted exclusively by the connecting section 6. There is, therefore, no further branch on this stretch which would extend in parallel and which would additionally transmit said tensile force. It is particularly preferred in this context that the tensile force exerted is at least sectionally completely transmitted by the plurality of threads 5a, 5b, 5c, wherein the at least sectionally complete transmission is to be understood as just described.

In this case, the connecting section 6 may have also been manufactured together with the central section 2 in a single manufacturing operation by means of a crochet galloon machine.

An optimal and balanced suspension is achieved when the band-like structure 1 is suspended on two fastening locations, wherein the corresponding lateral sections are each located on opposite sides of the central section 2. For this reason, it is provided in a preferred embodiment that the band-like structure 1 has a second connecting section 7 and a second lateral section 8, wherein a connecting section 6, 7 is respectively located between the central section 2 and the lateral sections 4, 8 such that a tensile force which is exerted on both the lateral sections 4, 8 is at least sectionally completely transmitted by the connecting sections 6, 7. It is preferred that the exerted tensile force is at least sectionally completely transmitted by the plurality of threads 5a, 5b, 5c. Again, the at least sectionally complete transmission is to be understood as described above.

Any statement applicable to the connecting section 6 is preferably valid also for the second connecting section 7. Similarly, each preferred feature of the lateral section 4 may likewise refer to the second lateral section 8.

As has already been described, it is to be assumed that the central section 2 and a lateral section 4 are contorted in relation to one another about the connecting section 6 during the surgical procedure for the implantation of the band-like structure 1. In order to absorb this contortion in a controlled manner, it is preferably provided that the connecting section 6, 7 has a contortion section 9 which consists of the plurality of threads 5a, 5b, 5c. Even further preferably, the plurality of threads 5a, 5b, 5c is separately guided within the contortion section 9. The separate guidance as individual threads 5a, 5b, 5c also readily allows a multiple contortion of the threads 5a, 5b, 5c without a force being exerted on the other parts of the band-like structure 1 as a result.

It is further preferred that the plurality of threads 5a, 5b, 5c sectionally forms a textile band 10, in which the plurality of threads 5a, 5b, 5c is interconnected by binding fibres 11. In particular, the textile band may consist of the plurality of threads 5a, 5b 5c and the textile band 10.

The textile band 10 may be a knit fabric, in particular a warp knit, which comprises the plurality of threads 5a, 5b, 5c. In this case, the binding fibers 11 also represent warp and weft threads of said warp knit. The said warp knit may again be one which has been manufactured in the same operation as the central knit fabric 2. When they are not separated from one another by a contortion section 9 consisting of the loose threads 5a, 5b, 5c, these knit fabrics and the central knit fabric 2a may also form a single contiguous knit fabric.

The contortion section 9 intended for the absorption of contortions, which has been described above, may in principle be executed having a relatively short length in comparison to the entire length of the connecting section 6, 7, since such a short length is quite sufficient for absorbing a plurality of contortions. The entire length of the connecting section 6, 7, however, depends on the anatomic distance which has to be bridged between the fraction point and the fastening locations. Said anatomic distance is, as a rule, relatively great. In order to limit the contortions now occurring to a specific region of the connecting section 6, 7, it is preferably provided that the connecting section 6, 7 has a transitional section 10a which consists of the textile band 10. Since the transitional section 10a has transverse connections between the plurality of threads 5a, 5b, 5c, a contortion may not readily occur here. These thus remain limited to the contortion section 9. The result is a defined behavior of the connecting section 6, 7.

In order to achieve a particularly good resilience to tension of the band-like structure 1, the plurality of threads 5a, 5b, 5c according to an advantageous embodiment forms warp threads 12 in the central knit fabric 2a. This is accompanied by the plurality of threads 5a, 5b, 5c extending along the central warp direction 3 in the central knit fabric 2a. Due to the manufacturing process, a warp knit is particularly resilient to tension exerted in the warp direction.

In order to obtain the already described advantages which are derived from a development of the central section 2 as a central knit fabric 2a in the same manner for the lateral sections 4, 8, it is provided according to a preferred embodiment that the lateral section 4, 8 has a lateral knit fabric 4a, 8a, which comprises the plurality of threads 5a, 5b, 5c. In this case, the inclusion of the plurality of threads 5a, 5b, 5c in the lateral knit fabric 4a, 8a is to be understood in the same sense as the already described inclusion of the plurality of threads 5a, 5b, 5c in the central knit fabric 2a. The lateral knit fabric 4a, 8a preferably consists of the plurality of threads 5a, 5b, 5c. It is also preferable that the plurality of threads 5a, 5b, 5c forms warp threads 12 in the lateral knit fabric 4a, 8a, as a result of which the abovementioned advantages in respect of the tensile load also occur here. It is particularly advantageous that the lateral knit fabric 4a, 8a comprises the binding fibers. This means that the binding fibers also form warp or weft threads of the lateral knit fabric 4a, 8a.

The lateral knit fabrics 4a, 8a may again be ones which have been manufactured in the same operation as the central knit fabric 2a. It applies to them, too, that when they are not separated from the central knit fabric 2a by a contortion section 9 consisting of the loose threads 5a, 5b, 5c, they may also form a single contiguous knit fabric with the central knit fabric 2a and optionally with a textile band 10 which forms a knit fabric.

The actual distance between the traction point and the fastening locations depends not only primarily on the organ to be supported and secondly on the special selection of the traction point and the fastening locations, but also on the size and the anatomic dimensions of the patient in each case. In order to design the band-like structure 1 to be suitable for a wide bandwidth of such limiting conditions, the lateral section 4, 8 is, as a rule, oversized in its length and thus allows an ad hoc cutting to size immediately prior to or even during the surgery. However, the actual measurement of length on the band-like structure 1 is difficult once the band-like structure 1 is located in the sub-peritoneal space. In order to provide the surgeon with an orientation location for initiating the cut to size, it is preferably provided that the plurality of threads 5a, 5b, 5c is arranged such that it forms markings 13 for identifying cutting or connecting locations. This may occur, for example, in that the plurality of threads 5a, 5b, 5c are of contrasting color to other components of the lateral section 4, 8, as is also illustrated in FIG. 1. The markings 13 then may in each case be formed by an irregular course of at least one of the plurality of threads 5a, 5b, 5c. According to the situation shown in FIG. 1, this may occur as a result of a sectionally offset arrangement in the weft direction of the peripherally located threads 5a, 5c. Therefore, instead of taking a direct measurement of the length, the surgeon may identify a specific cutting location by a specific number of markings 13 which have to be counted. In this case, the markings 13 are preferably spaced apart from one another at regular intervals.

These markings 13, however, not only serve for determining the cutting locations but may also identify those locations of the band-like structure 1 on which, precisely, the fastening has to be carried out. For example, in this manner a thread intended for a fastening by means of suturing or a staple may be guided through the band-like structure 1 at the location which is identified by such a marking 13.

An optimal tensile strength of the band-like structure 1 having at the same time the possibility of a very elegant and reliable manufacturing method lends itself when the band-like structure 1 has a common warp direction 3a. This then corresponds to the central warp direction 3. A common warp direction 3a may be achieved, for example, in that at least the textile parts of the band-like structure 1 form a warp knit which has been manufactured in a single operation on a crochet galloon machine.

It is preferred in this context that the plurality of threads 5a, 5b, 5c form warp threads along the band-like structure 1, that is to say in any case form warp threads along the textile part of the band-like structure 1. It is further preferred that all edges of the band-like structure 1 along the common warp direction 3a are genuine edges. A genuine edge is one which has no free-standing thread ends. By avoiding free-standing thread ends, the risk of injury caused by them to the surrounding tissue is also diminished.

The central section 2 preferably has rectangular mesh openings 14. According to a preferred embodiment, said mesh openings 14 are oriented along the central warp direction 3. This means that opposing pairs of sides of longitudinal webs of the rectangular mesh openings 14 extend parallel to the central warp direction 3. At the same time, opposing pairs of sides of transverse webs extend orthogonally to said central warp direction and, therefore, parallel to a weft direction 15. In the case of such an orientation of the individual meshes 14, these may also absorb greater tensile forces without substantially deforming or constricting. In this manner, the effective porosity of the central section 2 is preserved and it is ensured that ingrowth which has already occurred in the central section 2 by the surrounding tissue is not torn open again. The result is a connection of the band-like structure 1 with the tissue that occurs faster and is sustained.

Particular advantages occur when the rectangular mesh openings 14 are longer in the central warp direction 3 than in a weft direction 15 of the central section 2. The band-like structure 1 is primarily subjected to tensile loading in its main direction. As a result of the warp wales, which extend in the central warp direction 3, consisting mostly of multiple warp threads which are formed by loose threads, the central knit fabric 2a is particularly resilient to tension in this direction. For this reason, the distance between the transverse webs which form the rectangular mesh openings 14 can be chosen to be greater in the central warp direction 3 than the distance between the longitudinal webs in weft direction 15, without negatively affecting the tensile strength in the main direction of loading. As a result, the area of the mesh opening 14 is enlarged, which leads to an improved porosity and, in particular, to an improved effective porosity.

As has already been described, the band-like structure 1 is in each case guided through an opening into the peritoneum and out again. In order to facilitate this, it is preferably provided that the band-like structure 1 has a tube-shaped insertion aid 16 which is fastened to the lateral section 4. The tube-shaped form facilitates the passage through the opening into the peritoneum. The tube-shaped insertion aid 16 may, for example, envelop an end of the lateral section 4 in the manner of a shrink tubing and in this manner be connected to the lateral section 4. The tube-shaped insertion aid 16 on its part may also be connected to a pull thread 17 by which the tube-shaped insertion aid 16 and with it the entire band-like structure 1 may be pulled. The insertion aid 16 as well as the pull thread 17 are then severed by the cutting to size of the band-like structure 1 on the lateral section 4, and may then be removed. It is also preferred that the insertion aid 16 is connected to the plurality of threads 5a, 5b, 5c. In this manner, the tensile force exerted on the insertion aid 16 is immediately transferred to the components of the band-like structure 1 which are designed for the absorption of the tensile force.

The central section 2, the lateral section 4 and the plurality of threads 5a, 5b, 5c of the band-like structure 1 preferably consist of non-absorbable, bio-stable polyvinylidene fluoride (PVDF). It is further preferred that this also applies to the connecting section 6.

Furthermore preferred, the band-like structure 1 comprises at least one additive which is visible in magnetic resonance tomography. In principle, the material which is used in the manufacture of band-like structures intended for use as implants is not identifiable in magnetic resonance tomography. This also applies to PVDF. Due to the regular construction of the band-like structure 1 according to the proposal, the addition of substances which are visible in magnetic resonance tomography to even only a few threads is sufficient to make the presence of the band-like structure in the body evident. In this manner, the further progress of the therapy may be observed without having to resort to surgical intervention.

The invention claimed is:
1. Band-like structure for the augmentation of a ligament, comprising:
   a central section for fastening to an organ of the true pelvis;
   a lateral section for fastening to a suspension surface;
   a plurality of threads which are connected to the central section and the lateral section; and
   a connecting section comprising the plurality of threads;
   wherein the central section comprises a central knit fabric with a central warp direction;

wherein the central warp direction is parallel with an axis extending along the connecting section from the lateral section to the central section;

wherein the central knit fabric comprises the plurality of threads;

wherein the connecting section is located between the central section and the lateral section such that a tensile force exerted on the central section and the lateral section is at least sectionally completely transmitted by the connecting section;

wherein the connecting section comprises a contortion section which comprises the plurality of threads; and wherein the plurality of threads is separately guided within the contortion section.

2. Band-like structure according to claim 1, wherein the band-like structure comprises a second connecting section and a second lateral section; and wherein a connecting section is respectively located between the central section and the lateral sections such that a tensile force exerted on the two lateral sections is at least sectionally completely transmitted by the connecting sections.

3. Band-like structure according to claim 1, wherein the plurality of threads sectionally forms a textile band in which the plurality of threads is interconnected by binding fibers.

4. Band-like structure according to claim 3, wherein the connecting section comprises a transitional section which consists of the textile band.

5. Band-like structure according to claim 1, wherein the plurality of threads forms warp threads in the central knit fabric.

6. Band-like structure according to claim 1, wherein the lateral section comprises a lateral knit fabric.

7. Band-like structure according to claim 6, wherein the plurality of threads is arranged such that it forms markings.

8. Band-like structure according to claim 1, wherein the band-like structure comprises a common warp direction.

9. Band-like structure according to claim 1, wherein the central section comprises rectangular mesh openings.

10. Band-like structure according to claim 1, wherein the central section, the lateral section, the plurality of threads, and the connecting section consist of non-absorbable, biostable polyvinylidene fluoride.

11. Band-like structure according to claim 1, wherein the band-like structure comprises a tube-shaped insertion aid, which is fastened to the lateral section.

12. Band-like structure according to claim 1, comprising at least one additive which is visible in magnetic resonance tomography.

13. Band-like structure according to claim 1, wherein the tensile force is at least sectionally completely transmitted by the connecting section, by the plurality of threads.

14. Band-like structure according to claim 2, wherein the tensile force exerted on the two lateral sections is at least sectionally completely transmitted by the connecting sections by the plurality of threads.

15. Band-like structure according to claim 6, wherein the lateral knit fabric comprises the plurality of threads.

16. Band-like structure according to claim 15, wherein the plurality of threads forms warp threads in the lateral knit fabric.

17. Band-like structure according to claim 7, wherein the markings are spaced in a regular manner, for identifying cutting or connecting locations.

18. Band-like structure according to claim 8, wherein the plurality of threads form warp threads along the band-like structure.

19. Band-like structure according to claim 9, wherein the rectangular mesh openings are oriented along the central warp direction.

20. Band-like structure according to claim 11, wherein the insertion aid is connected to the plurality of threads.

21. Band-like structure according to claim 16, wherein the lateral knit fabric comprises binding fibers.

22. Band-like structure according to claim 18, wherein all edges of the band-like structure along the common warp direction are genuine edges.

23. Band-like structure according to claim 19, wherein the rectangular mesh openings are longer in the central warp direction than in a weft direction of the central section.

* * * * *